United States Patent
Jeung et al.

(10) Patent No.: US 9,119,541 B2
(45) Date of Patent: *Sep. 1, 2015

(54) EYEWEAR FOR PATIENT PROMPTING

(75) Inventors: Andrew G. Jeung, Mountain View, CA (US); Hassan Mostafavi, Los Altos, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/716,232

(22) Filed: Mar. 2, 2010

(65) Prior Publication Data

US 2010/0158198 A1    Jun. 24, 2010

Related U.S. Application Data

(63) Continuation of application No. 11/217,789, filed on Aug. 30, 2005, now abandoned.

(51) Int. Cl.
| | | |
|---|---|---|
| *A61B 5/00* | (2006.01) | |
| *A61B 6/03* | (2006.01) | |
| *A61B 5/113* | (2006.01) | |

(52) U.S. Cl.
CPC    *A61B 6/032* (2013.01); *A61B 5/113* (2013.01)

(58) Field of Classification Search
CPC ............... A61M 2016/0036; A61M 16/00; A61M 2205/583; A61B 5/087; A61B 5/1135; A61B 5/7264; A61B 5/097; A61B 5/7285; A61B 5/091; A61B 5/113
USPC ......... 600/425, 427, 428; 378/4, 8, 20, 95, 98
See application file for complete search history.

(56) References Cited

U.S. PATENT DOCUMENTS

| 3,861,807 | A | 1/1975 | Lescrenier |
| 3,871,360 | A | 3/1975 | Van Horn et al. |
| 3,952,201 | A | 4/1976 | Hounsfield |
| 4,031,884 | A | 6/1977 | Henzel |
| 4,262,306 | A | 4/1981 | Renner |

(Continued)

FOREIGN PATENT DOCUMENTS

| DE | 4341324 | 6/1995 |
| DE | 19856467 | 5/2000 |

(Continued)

OTHER PUBLICATIONS

Adams, W.B. et al. "Correlator Compensation Requirements for Passive Time-Delay Estimation with Moving Source or Receivers" IEEE Transactions on Acoustics, Speech and Signal Processing (Apr. 1980) ASSP 28(2):158-168.

(Continued)

*Primary Examiner* — Elmer Chao
(74) *Attorney, Agent, or Firm* — Vista IP Law Group, LLP

(57) ABSTRACT

An apparatus for prompting a patient includes a structure configured to be mounted to a patient support, a screen coupled to the structure, and a projector located at a distance away from the screen. A method of prompting a patient that is being supported on a patient support includes adjusting a position of a screen relative to a projector, the screen having a surface, placing the screen in front of the patient such that the patient can see the surface, and providing an image on the screen using the projector.

43 Claims, 8 Drawing Sheets

(56) References Cited

U.S. PATENT DOCUMENTS

| | | | |
|---|---|---|---|
| 4,463,425 A | 7/1984 | Hirano et al. | |
| 4,710,717 A | 12/1987 | Pele et al. | |
| 4,804,261 A * | 2/1989 | Kirschen | 351/158 |
| 4,853,771 A | 8/1989 | Witriol et al. | |
| 4,895,160 A | 1/1990 | Reents | |
| 4,971,065 A | 11/1990 | Pearce | |
| 4,984,158 A * | 1/1991 | Hillsman | 128/200.14 |
| 4,994,965 A | 2/1991 | Crawford et al. | |
| 5,080,100 A | 1/1992 | Trotel | |
| 5,271,055 A | 12/1993 | Hsieh et al. | |
| 5,279,309 A | 1/1994 | Taylor et al. | |
| 5,295,483 A | 3/1994 | Nowacki et al. | |
| 5,315,630 A | 5/1994 | Sturm et al. | |
| 5,363,844 A | 11/1994 | Riederer et al. | |
| 5,389,101 A | 2/1995 | Heilbrun et al. | |
| 5,394,875 A | 3/1995 | Lewis et al. | |
| 5,414,459 A * | 5/1995 | Bullwinkel | 348/53 |
| 5,446,548 A | 8/1995 | Gerig et al. | |
| 5,482,042 A * | 1/1996 | Fujita | 600/428 |
| 5,506,705 A | 4/1996 | Yamamoto et al. | |
| 5,513,646 A | 5/1996 | Lehrman et al. | |
| 5,538,494 A | 7/1996 | Matsuda | |
| 5,565,777 A | 10/1996 | Kanayama et al. | |
| 5,582,182 A | 12/1996 | Hillsman | |
| 5,588,430 A | 12/1996 | Bova et al. | |
| 5,603,318 A | 2/1997 | Heilbrun et al. | |
| 5,619,995 A | 4/1997 | Lobodzinski | |
| 5,622,187 A | 4/1997 | Carol | |
| 5,638,819 A | 6/1997 | Manwaring et al. | |
| 5,662,111 A | 9/1997 | Cosman | |
| 5,662,112 A | 9/1997 | Heid | |
| 5,714,884 A | 2/1998 | Hoshino | |
| 5,727,554 A | 3/1998 | Kalend et al. | |
| 5,764,723 A | 6/1998 | Weinberger et al. | |
| 5,771,310 A | 6/1998 | Vannah | |
| 5,784,431 A | 7/1998 | Kalend et al. | |
| 5,794,621 A | 8/1998 | Hogan et al. | |
| 5,806,116 A | 9/1998 | Oliver et al. | |
| 5,820,553 A | 10/1998 | Hughes | |
| 5,823,192 A | 10/1998 | Kalend et al. | |
| 5,825,563 A | 10/1998 | Ananad | |
| 5,836,954 A | 11/1998 | Heilbrun et al. | |
| 5,861,865 A | 1/1999 | Anand et al. | |
| 5,906,202 A | 5/1999 | Schuster et al. | |
| 5,912,656 A | 6/1999 | Tham et al. | |
| 5,954,647 A | 9/1999 | Bova et al. | |
| 5,993,397 A | 11/1999 | Branson | |
| 5,997,439 A | 12/1999 | Ohsuga et al. | |
| 6,076,005 A | 6/2000 | Sontag et al. | |
| 6,138,302 A | 10/2000 | Sashin et al. | |
| 6,144,874 A | 11/2000 | Du | |
| 6,144,875 A | 11/2000 | Schweikard et al. | |
| 6,146,390 A | 11/2000 | Heibrun et al. | |
| 6,165,181 A | 12/2000 | Heibrun et al. | |
| 6,185,445 B1 | 2/2001 | Knuttel | |
| 6,185,446 B1 | 2/2001 | Carlsen | |
| 6,198,959 B1 | 3/2001 | Wang | |
| 6,272,368 B1 | 8/2001 | Alexandrescu | |
| 6,292,305 B1 | 9/2001 | Sakuma et al. | |
| 6,296,613 B1 | 10/2001 | Emmenegger et al. | |
| 6,300,974 B1 | 10/2001 | Viala et al. | |
| 6,307,914 B1 | 10/2001 | Kunieda et al. | |
| 6,348,058 B1 | 2/2002 | Melkent et al. | |
| 6,370,217 B1 | 4/2002 | Hu et al. | |
| 6,405,072 B1 | 6/2002 | Cosman | |
| 6,434,507 B1 | 8/2002 | Clayton et al. | |
| 6,473,635 B1 | 10/2002 | Rasche | |
| 6,501,981 B1 | 12/2002 | Schweikard et al. | |
| 6,527,443 B1 | 3/2003 | Vilsmeier et al. | |
| 6,611,617 B1 | 8/2003 | Crampton | |
| 6,621,889 B1 | 9/2003 | Mostafavi | |
| 6,665,370 B2 | 12/2003 | Bruder et al. | |
| 6,724,930 B1 | 4/2004 | Kosaka et al. | |
| 7,182,083 B2 | 2/2007 | Yanof et al. | |
| 7,778,691 B2 * | 8/2010 | Zhang et al. | 600/427 |
| 7,783,335 B2 * | 8/2010 | Le Corre | 600/407 |
| 2002/0023652 A1 | 2/2002 | Riaziat et al. | |
| 2003/0007593 A1 | 1/2003 | Heuscher et al. | |
| 2003/0063292 A1 | 4/2003 | Mostafavi | |
| 2003/0072419 A1 | 4/2003 | Bruder et al. | |
| 2003/0188757 A1 | 10/2003 | Yanof et al. | |
| 2003/0190010 A1 | 10/2003 | Tsujii | |
| 2003/0210812 A1 | 11/2003 | Khamene et al. | |
| 2004/0005088 A1 | 1/2004 | Jeung et al. | |
| 2004/0030235 A1 | 2/2004 | Sasaki et al. | |
| 2004/0071337 A1 | 4/2004 | Jeung et al. | |
| 2004/0082853 A1 | 4/2004 | Sasaki et al. | |
| 2004/0116804 A1 | 6/2004 | Mostafavi | |
| 2004/0218719 A1 | 11/2004 | Brown et al. | |
| 2004/0254773 A1 | 12/2004 | Zhang et al. | |
| 2005/0119560 A1 | 6/2005 | Mostafavi | |
| 2005/0283068 A1 | 12/2005 | Zuccolotto et al. | |
| 2006/0074286 A1 | 4/2006 | Miller et al. | |
| 2006/0074305 A1 | 4/2006 | Mostafavi | |
| 2006/0079763 A1 | 4/2006 | Jeung et al. | |
| 2006/0129044 A1 | 6/2006 | Le Corre | |

FOREIGN PATENT DOCUMENTS

| | | |
|---|---|---|
| EP | 1050272 | 11/2000 |
| FI | 79458 | 9/1989 |
| JP | 2000262511 | 9/2000 |
| JP | 2000325339 | 11/2000 |
| JP | 2002090118 | 3/2002 |
| JP | 2004-000412 A | 1/2004 |
| WO | 9816151 | 4/1998 |
| WO | 9830977 | 7/1998 |
| WO | 9838908 | 9/1998 |
| WO | 9852635 | 11/1998 |
| WO | 0024333 | 5/2000 |
| WO | 02085455 | 10/2002 |
| WO | 03/003796 A1 | 1/2003 |
| WO | 03003796 | 1/2003 |
| WO | 2006/039394 | 4/2006 |

OTHER PUBLICATIONS

Ahlström, K.H. et al "Pulmonary MR Angiography with Ultrasmall Superparamagnetic Iron Oxide Particles as a Blood Pool Agent and a Navigator Echo for Respiratory Gating: Pilot Study" Radiology (Jun. 1999) 211(3):865-869.

Axel, L. et al. "Respiratory Effects in Two-Dimensional Fourier Transform MR Imaging" Radiology (Sep. 1986) 160(3):795-801.

Balter, J.M. et al. "Uncertainties in CT-Based Radiation Therapy Treatment Planning Associated with Patient Breathing" Int. J. Radiation Oncology Biol. Phys. (Aug. 1, 1996) 36(1):167-174.

Bankman, I.N. et al. "Optimal Detection, Classification, and Superposition Resolution in Neural Waveform Recordings" IEEE Transactions on Biomedical Engineering (Aug. 1993) 40(8):836-841.

Baroni, G. and G. Ferrigno "Real-time Motion Analysis for Definition and Control of Patient Position in Radiotherapy" Proc. SPIE Medical Imaging 1996: Physiology and Function from Multidimensional Images (Apr. 1996) 2709:506-515.

Bellenger, N. G. et al. "Left Ventricular Quantification in Heart Failure by Cardiovascular MR Using Prospective Respiratory Navigator Gating: Comparison with Breath-Hold Acquisition" Journal of Magnetic Resonance Imaging (Apr. 2000) 11(4):411-417.

Cho.K. et al. "Development of Respiratory Gated Myocardial SPECT System" J. Nuci. Cardiol. (Jan./Feb. 1999) 6(1):20-28.

Danias, P.G. et al. "Prospective Navigator Correction of Image Position for Coronary MR Angiography" Radiology (Jun. 1997) 203:733-736.

Davies, S.C. et al. "Ultrasound Quantitation of Respiratory Organ Motion in the Upper Abdomen" Br. J. Radiol. (Nov. 1994) 67(803):1096-1102.

Du, Y.P. "Prospective navigator gating with a dual acceptance window technique to reduce respiratory motion artifacts in 3D MR coronary angiography" Int'l J. Cardiovascular Imaging (2003) 19:157-162.

Du, Y.P. et al. "A comparison of prospective and retrospective respiratory navigator gating in 3D MR coronary angiography" Int'l J.

(56) References Cited

OTHER PUBLICATIONS

Cardiovascular Imaging (2001) 17:287-294.
Ehman, R.L. et al. "Magnetic Resonance Imaging with Respiratory Gating: Techniques and Advantages" AJR (Dec. 1984) 143:1175-1182.
Fee, M.S. et al. "Automatic Sorting of Multiple Unit neuronal Signals in the Presence of Anisotropic and non-Gaussian Variability" J. Neuroscience Methods (1996) 69:175-188.
Felblinger, J. et al. "Effects of physiologic motion of the human brain upon quantitative 1H-MRS: analysis and correction by retrogating" NMR in Biomedicine (1998) 11:107-114.
Fishbein, K.W. et al. "The lever-coil: a simple, inexpensive sensor for respiratory and cardiac in MRI experiments" Magnetic Resonance Imaging (2001) 19:881-889.
Frölich, H. et al. "A Simple Device for Breath-Level Monitoring During CT" Radiology (Jul. 1985) 156(1):235.
Gerig, L.H. et al. "The Development and Clinical Application of a Patient Position Monitoring System" Proc. SPIE Videometrics III (Oct. 1994) 2350:59-72.
Haacke, E.M. and G.W. Lenz "Improving MR Image Quality in the Presence of Motion by Using Rephasing Gradients" AJR (Jun. 1987) 148:1251-1258.
Hanley, J. et al. "Deep Inspiration Breath-Hold Technique for Lung Tumors: The Potential Value of Target Immobilization and Reduced Lung Density in Dose Escalation" Int. J. Radiation Oncology biol. Phys. (Oct. 1, 1999) 45(3):603-611.
Henkelman, R.M. and K. Mah "How Important is Breathing in Radiation Therapy of the Thorax?" Int. J. Radiation Oncology Biol. Phys. (Nov. 1982) 8(11):2005-2010.
Hofman, M.B.M. et al. "MRI of Coronary Arteries: 2D Breath-Hold vs. 3D Respiratory-Gated Acquisition" J. Computer Assisted Tomography (Jan./Feb. 1995) 19(1):56-62.
Huber, A. et al. "Navigator Echo-Based Respiratory Gating for Three-Dimensional MR Coronary Angiography: Results from Healthy Volunteers and Patients with Proximal Coronary Artery Stenoses" AJR (Jul. 1999) 173:95-101.
Iwasawa, T. et al. "Normal In-Plane Respiratory Motion of the Bilateral Hemidiaphragms Evaluated by Sequentially Subtracted Fast Magnetic Resonance Images" Journal of Thoracic Imaging (1999) 14(2):130-134.
Johnson, L.S. et al. "Initial Clinical Experience with a Video-Based Patient Positioning System" Int. J. Radiation Oncology Biol. Phys. (Aug. 1, 1999) 45(1):205-213.
Jolesz, F. "Image-guided Procedures and the Operating Room of the Future" Radiology (May, 1997) 204:601-612.
Josefsson, T. et al. "A Flexible High-Precision Video System for Digital Recording of Motor Acts Through Lightweight Reflex Markers" Computer Methods & Programs in Biomedicine (1996) 49:119-129.
Kachelriess, M. and W.A. Kalender "Electrocardiogram-Correlated Image Reconstruction from Subsecond Spiral Computed Tomography Scans of the Heart" Med. Phys. (Dec. 1998) 25(12):2417-2431.
Keatley, E. et al "Computer Automated Diaphragm Motion Quantification in a Fluoroscopic Movie" Proceedings of the 22nd Annual International Conference of the IEEE Engineering in Medicine and Biology Society, Chicago, IL (Jul. 23-28, 2000) 3:1749-1751.
Kim, W.S., et al. "Extraction of Cardiac and Respiratory Motion Cycles by Use of Projection Data and its Applications NMR Imaging" Magnetic Resonance in Medicine (1990) 13:25-37.
Korin, H.W. et al. "Respiratory Kinematics for the Upper Abdominal Organs: A Quantitative Study" Magnetic Resonance in Medicine (Jan. 1992) 23(1):172-178.
Kubo, H.D. and L. Wang "Compatibility of Varian 2100C Gated Operations with Enhanced Dynamic Wedge and IMRT Dose Delivery" Med. Phys. (Aug. 2000) 27(8):1732-1738.
Kubo, H.D. et al. "Respiration Gated Radiotherapy Treatment: A Technical Study" Phys. Med. Biol. (1996) 41:83-91.

Kubo, H.D. et al. "Breathing-Synchronized Radiotherapy Program at the University of California Davis Cancer Center" Med. Phys. (Feb. 2000) 27(2):346-353.
Kubo, H.D. et al. "Potential and Role of a Prototype Amorphous Silicon Array Electronic Portal Imaging Device in Breathing Synchronized Radiotherapy" Med. Phys. (Nov. 1999) 26(11):2410-2414.
Kutcher, G.J. et al. "Control, Correction, and Modeling of Setup Errors and Organ Motion" Seminars in Radiation Oncology. (Apr. 1995) 5(3):134-145.
Lee, M.W. and I. Cohen "Human Body Tracking with Auxiliary Measurements" IEEE International Workshop on Analysis and Modeling of Faces and Gestures (2003) 8 pgs., located at http://iris.usc.edu/~icohen/projects/human/body/index.htm.
Leiberman, J.M. et al. "Gated Magnetic Resonance Imaging of the Normal Diseased Heart" Radiology (Aug. 1984) 152:465-470.
Lethimonnier, F. et al. "Three-Dimensional Coronary Artery MR Imaging Using Prospective Real-Time Respiratory Navigator and Linear Phase Shift Processing: Comparison with Conventional Coronary Angiography" Magnetic Resonance Imaging (1999) 17(8):1111-1120.
Lewis, C.E. et al. "Comparison of Respiratory Triggering and Gating Techniques for the Removal of Respiratory Artifacts in MR Imaging" Radiology (Sep. 1986) 160(3):803-810.
Li, D. et al. "Coronary Arteries: Three-Dimensional MR Imaging with Retrospective Respiratory Gating" Radiology (Dec. 1996) 201(3):857-863.
Lopresti, B.J. et al. "Implementation and Performance of an Optical Motion Tracking System for High Resolution Brain PET Imaging" IEEE Transactions on Nuclear Science (Dec. 1999) 46(6):2059-2067.
Luker, G.D. et al. "Ghosting of Pulmonary Nodules with Respiratory Motion: Comparison of Helical and Conventional CT Using and in Vitro Pediatric Model" AJR (Nov. 1996) 167:1189-1193.
Mageras, G. et al. "Initial Clinical Evaluation of a Respiratory Gating Radiotherapy System" in 22nd Annual EMBS International Conference, Chicago, IL (Jul. 23-28, 2000) pp. 2124-2127.
Mageras, G.S. "Interventional Strategies for Reducing Respiratory-Induced Motion in External Beam Therapy" The Use of Computers in Radiation Therapy, XIIIth International Conference, Heidelberg, Germany (May 22-25, 2000) pp. 514-516.
Mageras, G.S. et al. "Respiratory Motion-Induced Treatment Uncertainties" Patras Medical Physics 99—VI International Conference on Medical Physics, Patras (Greece) (Sep. 1-4, 1999) pp. 33-39.
Mah, D. et al. "Technical Aspects of the Deep Inspiration Breath-Hold Technique in the Treatment of Thoracic Cancer" Int. J. Radiation Oncology Biol. Phys. (Nov. 1, 2000) 48(1):1175-1185.
Mah, K. and R.M. Henkelman "Time Varying Dose Due to Respiratory Motion During Radiation Therapy of the Thorax"; Proceedings of the Eighth Int'l Conference on the Use of Computers in Radiation Therapy, Toronto, Canada (Jul. 9-12, 1984) pp. 294-298.
Malone, S. et al. "Respiratory-Induced Prostate Motion: Quantification and Characterization" Int. J. Radiation Oncology Biol. Phys. (Aug. 2000) 48:105-109.
Manke, D. et al. "Model Evaluation and Calibration for Prospective Respiratory Motion Correction in Coronary MR Angiography Based on 3-D Image Registration" IEEE Transactions on Medical Imaging (Sep. 2002) 21(9):1132-1141.
Manke, D. et al. "Respiratory Motion in Coronary Magnetic Resonance Angiography: A Comparison of Different Motion Models" J. Magnetic Resonance Imaging (2202) 14:661-671.
McConnell, M.V. et al. "Comparison of Respiratory Suppression Methods and Navigator Locations for MR Coronary Angiography" AJR (May 1997) 168:1369-1375.
McConnell, M.V. et al. "Prospective Adaptive Navigator Correction for Breath-Hold MR Coronary Angiography" MRM (1997) 37:148-152.
Moerland, M.A. et al. "The Influence of Respiration Induced Motion of the Kidneys on the Accuracy of Radiotherapy Treatment Planning, a Magnetic Resonance Imaging Study" Radiotherapy and Oncology (1994) 30:150-154.

(56) References Cited

OTHER PUBLICATIONS

Mori, M. et al. "Accurate Contiguous Sections Without Breath-Holding on Chest CT: Value of Respiratory Gating and Ultrafast CT" AJR (May 1994) 162:057-1062.
Nevatia, R. et al. "Human Body Tacking with Articulated Human Body Model" (Nov. 2002) pp. 1-3 located at http://www.scf.usc.edu/~munlee/humanBodyTrk.html.
Nikolaou, K. et al. "Navigator Echo-Based Respiratory Gating for Three-Dimensional MR Coronary Angiography: Reduction of Scan Time Using a Slice Interpolation Technique" J. Computer Assisted Tomography (2001) 25(3):378-387.
Ohara, K. et al. "Irradiation Synchronized with Respiration Gate" Int. J. Radiation Oncology Biol. Phys. (Oct. 1989) 17(4):853-857.
Oshinski, J.N. et al. "Two-Dimensional Coronary MR Angiography Without Breath-Holding" Radiology (Dec. 1996) 201(3):737-743.
Paradis, A.L. et al. "Detection of Periodic Signals in Brain Echo-Planar Functional Images" Proceedings of the 18th Annual International Conference of the IEEE Engineering in Medicine and Biology Society, Amsterdam, The Netherlands (1996) pp. 696-697.
Peltola, S. "Gated Radiotherapy to Compensate for Patient Breathing" Proceedings of the Eleventh Varian Users Meeting, Marco Island, Florida (May 11-13, 1986) 3 pgs.
Plein, S. et al. "Three-Dimensional Coronary MR Angiography Performed with Subject-Specific Cardiac Acquisition Windows and Motion-Adapted Respiratory Gating" AJR (Feb. 2003) 180:505-512.
Post, J.C. et al. "Three-Dimensional Respiratory-Gated MR Angiography of Coronary Arteries: Comparison with Conventional Coronary Angiography" AJR (Jun. 1996) 166:1399-1404.
Ramsey, C.R. et al. "A Comparison of Beam Characteristics for Gated and Nongated Clinical X-Ray Beams" Med. Phys. (Oct. 1999) 26(10):2086-2091.
Ramsey, C.R. et al. "Clinical Efficacy of Respiratory Gated Conformal Radiation Therapy" Medical Dosimetry (1999) 24(2):115-119.
Regenfus, M. et al. "Comparison of Contrast-Enhanced Breath-Hold and Free-Breathing Respiratory-Gated Imaging in Three-Dimensional Magnetic Resonance Coronary Angiography" Am. J. Cardiology (Oct. 1, 2002) 90:725-730.
Ritchie, C.J. et al. "Predictive Respiratory Gating: A New Method to Reduce Motion Artifacts on CT Scans" Radiology (Mar. 1994) 190(3):847-852.
Robinson, T.E. et al. "Standardized High-Resolution CT of the Lung Using a Spirometer-Triggered Electron Beam CT Scanner" AJR (Jun. 1999) 172:1636-1638.
Rogus, R.D. et al. "Accuracy of a Photogrammetry-Based Patient Positioning and Monitoring System for Radiation Therapy" Med. Phys. (May 1999) 26(5):721-728.
Rosenzweig, K.E. et al. "The Deep Inspiration Breath-Hold Technique in the Treatment of Inoperable Non Small Cell Lung Cancer" Int. J. Radiation Oncology Biol. Phys. (Aug. 1, 2000) 48(1):81-87.
Ross, C.S et al. "Analysis of Movement of Intrathoracic Neoplasms Using Ultrafast Computerized Tomography" Int. J. Radiation Oncology Biol. Phys. (Mar. 1990) 18(3):671-677.
Runge, V.M. et al. "Respiratory Gating in Magnetic Resonance Imaging at 0.5 Tesla" Radiology (May 1984) 151(2):521-523.
Sachs, T.S. et al. "Real-Time Motion Detection in Spiral MRI Using Navigators" Magnetic Resonance in Medicine (Nov. 1994) 32(5):639-645.
Schär, M. et al. "The Impact of Spatial Resolution and Respiratory Motion on MR Imaging of Atherosclerotic Plaque" J. Magnetic Resonance Imaging (2003) 17:538-544.
Schwartz, L.H. et al. "Kidney Mobility During Respiration" Radiotherapy and Oncology. (1994) 32:84-86.
Shirato, H. et al. "Four-Dimensional Treatment Planning and Fluroscopic Real-Time Tumor Tracking Radiotherapy for Moving Rumor" Int. J. Radiation Oncology Biol. Phys. (Sep. 1, 2000) 48(2):435-442.
Sinkus, R. and P. Börnert "Motion Pattern Adapted Real-Time Respiratory Gating" Magnetic Resonance in Medicine (1999) 41:148-155.
Solberg, T.D. et al. "Feasibility of Gated IMRT" Proceedings of the 22nd annual International Conference of the IEEE Engineering in Medicine and Biology Society, Chicago, IL (Jul. 23-28, 2000) 4:2732-2734.
Spuentrup, E. et al. "Respiratory motion artifact suppression in diffusion-weighted MR imaging of the spine" Eur. Radiol. (2003) 13:330-336.
Suramo, I. et al. "Cranio-Caudal Movements of the Liver, Pancreas and Kidneys on Respiration" Acta Radiology Diagnosis (1984) 25(2):129-131.
Tada, T. et al. "Lung Cancer: Intermittent Irradiation Synchronized with Respiratory Motion-Results of a Pilot Study" Radiology (Jun. 1998) 207(3):779-783.
Thickman, D. et al. "Phase-Encoding Direction upon Magnetic Resonance Image Quality of the Heart" Magnetic Resonance in Medicine (1998) 6:390-396.
van Geuns, R.J.M. et al. "Magnetic Resonance Imaging of the Coronary Arteries: Clinical Results from Three Dimensional Evaluation of a Respiratory Gated Technique" Heart (Oct. 1999) 82(4):515-519.
Wang Y. et al. "Navigator-Echo-based Real-Time Respiratory Gating and Triggering for Reduction of Respiration Effects in Three-dimensional Coronary MR Angiography" Radiology (1996) 198:55-60.
Wang, Y. et al. "Respiratory Motion of the Heart: Kinematics and the Implications for the Spatial Resolution in Coronary Imaging" Magnetic Resonance in Medicine (1995) 33:713-719.
Weber, C. et al. "Correlation of 3D MR coronary angiography with selective coronary angiography: feasibility of the motion adapted gating technique" Eur. Radiol. (2002) 12:718-726.
Weiger, M. et al. "Motion-Adapted Gating Based on k-Space Weighting for Reduction of Respiratory Motion Artifacts" Magnetic Resonance in Medicine (Aug. 1997) 38(2):322-333.
Wiesmann, F. "High-Resolution MRI with Cardiac and Respiratory Gating Allows for Accurate in Vivo Atherosclerotic Plaque Visualization in Murine Aortic Arch" Magnetic Resonance in Medicine (2003) 50:69-74.
Wong, J.W. et al. "The Use of Active Breathing Control (ABC) to Reduce Margin for Breathing Motion" Int. J. Radiation Oncology Biol. Phys. (Jul. 1, 1999) 44(4):911-919.
Wood, M.L. and R.M. Henkelman "Suppression of respiratory motion artifacts in magnetic resonance imaging" Med. Phys. (Nov./Dec. 1996) 13(6):794-805.
Woodard, P.K. et al. "Detection of Coronary Stenoses on Source and Projection Images Using Three-Dimensional MR Angiography with Retrospective Respiratory Gating: Preliminary Experience" AJR (Apr. 1998) 170(4):883-888.
Worthley, S.G. et al. "Cardiac gated breath-hold back blood MRI of the coronary artery wall: An in vivo and ex vivo comparison" Int'l J. Cardiovascular Imaging (2001) 17:195-201.
Yamashita, Y. et al. "MR Imaging of Focal Lung Lesions: Elimination of Flow and Motion Artifacts by Breath-Hold ECG-Gated and Black-Blood Techniques on T2-Weighted Turbo SE and STIR Sequences" J. Magnetic Resonance Imaging (1999) 9:691-698.
Yorke, Ellen et al "Respiratory Gating of Sliding Window IMRT" Proceedings of the 22nd Annual International Conference of the IEEE Engineering in Medicine and Biology Society, Chicago, IL (Jul. 23-28, 2000) 3:2118-2121.
Yuan, Q. et al. "Cardiac-Respiratory Gating Method for Magnetic Resonance Imaging of the Heart" Magnetic Resonance in Medicine (Feb. 2000) 43:314-318.
Preliminary Search Brochure entitled "Kinematic Measurement Systems" by Qualisys printed Apr. 4, 1994.
http://en.wikipedia.org/wiki/Frogger.
International Search Report and Written Opinion dated Feb. 5, 2007 for PCT/US2005/034999.
Supplementary European Search Report dated Aug. 28, 2008 for EP05803610.
Notification of the First Office Action dated May 9, 2008 for CN200580039470.8.
Notification of the Second Office Action dated Oct. 31, 2008 for CN200580039470.8.
Notification of the Third Office Action dated Apr. 10, 2009 for CN200580039470.8.

(56) References Cited

OTHER PUBLICATIONS

Non-Final Office Action dated Jan. 22, 2009 for U.S. Appl. No. 10/956,199.
Non-Final Office Action dated Jan. 10, 2008 for U.S. Appl. No. 10/956,199.
Non-Final Office Action dated Mar. 23, 2007 for U.S. Appl. No. 10/956,199.
Non-Final Office Action dated Sep. 29, 2010 for U.S. Appl. No. 12/843,764.
Final Office Action dated Apr. 22, 2011 for U.S. Appl. No. 12/843,764.
Non-Final Office Action dated Sep. 12, 2011 for U.S. Appl. No. 12/843,764.
Notice of Allowance dated Feb. 10, 2012 for U.S. Appl. No. 12/843,764.
Final Notice of Reasons for Refusal dated Mar. 22, 2012 for JP Patent Application No. 2007-534756.
English Translation of Final Notice of Reasons for Refusal dated Mar. 22, 2012 for JP Patent Application No. 2007-534756.
Notice of Reasons for Refusal dated Feb. 12, 2013 for JP Patent Application No. 2007-534756.
English Translation of Notice of Reasons for Refusal dated Feb. 12, 2013 for JP Patent Application No. 2007-534756.
Decision of Registration dated Aug. 22, 2013 for JP Patent Application No. 2007-534756.
European Office Action dated Jun. 5, 2013 for EP Patent Application No. EP 05 803 610.4.
JP Notice of Publication dated Dec. 18, 2013 for JP Patent Application No. 2007-534756.
Final Office Action dated Aug. 3, 2009 for U.S. Appl. No. 10/956,199.
Final Office Action dated Oct. 5, 2007 for U.S. Appl. No. 10/956,199.
Final Office Action dated Oct. 15, 2009 for U.S. Appl. No. 10/956,199.
Non-Final Office Action dated Aug. 18, 2009 for U.S. Appl. No. 11/217,789.
Non-Final Office Action dated Oct. 6, 2008 for U.S. Appl. No. 11/217,789.
Final Office Action dated Apr. 23, 2009 for U.S. Appl. No. 11/217,789.
Advisory Action dated Jul. 10, 2009 for U.S. Appl. No. 11/217,789.
Non-Final Office Action dated Jan. 26, 2009 for U.S. Appl. No. 10/957,009.
Non-Final Office Action dated Dec. 18, 2006 for U.S. Appl. No. 10/957,009.
Non-Final Office Action dated Dec. 30, 2005 for U.S. Appl. No. 10/957,009.
Final Office Action dated Jul. 8, 2009 for U.S. Appl. No. 10/957,009.
Final Office Action dated Apr. 17, 2008 for U.S. Appl. No. 10/957,009.
Final Office Action dated Oct. 4, 2007 for U.S. Appl. No. 10/957,009.
Advisory Action dated Aug. 29, 2008 for U.S. Appl. No. 10/957,009.
Advisory Action dated Dec. 11, 2007 for U.S. Appl. No. 10/957,009.
Notice of Allowance dated Mar. 24, 2010 for U.S. Appl. No. 10/957,009.

* cited by examiner

EYEWEAR FOR PATIENT PROMPTING

This application is a continuation of U.S. patent application Ser. No. 11/217,789, filed on Aug. 30, 2005, the entire disclosure of which is expressly incorporated by reference herein.

RELATED APPLICATION DATA

This application is a continuation-in-part of U.S. patent application Ser. No. 10/956,199, filed Sep. 30, 2004, entitled "Patient Multimedia Display", the entire disclosure of which is expressly incorporated by reference herein.

This application is related to U.S. patent application Ser. No. 10/957,009, filed Sep. 30, 2004, entitled "Patient Visual Instruction Techniques For Synchronizing Breathing With a Medical Procedure", the entire disclosure of which is expressly incorporated by reference herein.

BACKGROUND OF THE INVENTION

1. Field of the Invention

This invention relates generally to systems and methods for prompting patient, and more specifically, to systems and methods for prompting patient to control patient movement.

2. Background of the Invention

Computed tomography is an imaging technique that has been widely used in the medical field. In a procedure for computed tomography, an x-ray source and a detector apparatus are positioned on opposite sides of a portion of a patient under examination. The x-ray source generates and directs a x-ray beam towards the patient, while the detector apparatus measures the x-ray absorption at a plurality of transmission paths defined by the x-ray beam during the process. The detector apparatus produces a voltage proportional to the intensity of incident x-rays, and the voltage is read and digitized for subsequent processing in a computer. By taking thousands of readings from multiple angles around the patient, relatively massive amounts of data are thus accumulated. The accumulated data are then analyzed and processed for reconstruction of a matrix (visual or otherwise), which constitutes a depiction of a density function of the bodily section being examined. By considering one or more of such sections, a skilled diagnostician can often diagnose various bodily ailments such as tumors, blood clots, etc.

Computed tomography has found its principal application to examination of bodily structures or the like which are in a relatively stationary condition. However, currently available computed tomographic apparatus may not be able to generate tomographic images with sufficient quality or accuracy due to physiological movement of a patient. For example, beating of a human heart and breathing have been known to cause degradation of quality in CT images.

Degradation of quality of CT images due to patient's breathing is more difficult to address than that associated with heart motion. Patients' breathing poses a unique problem to CT imaging that is different from heart motion. This is because the pattern and the period of a patient's breathing cycle is generally less consistent when compared to those of the patient's cardiac cycle. As such, while a particular phase of a cardiac cycle may be predicted with sufficient accuracy, a particular phase of a breathing cycle may not be as easily predicted or determined. Furthermore, there has been an increased desire to visualize organ motion by viewing a sequence of CT images as a movie sequence. However, collecting a large quantity of CT image data sufficient for forming a video while considering breathing motion is difficult to perform and may take a much longer time.

For the foregoing, it would be desirable to prompt a patient to control the patient's breathing as CT image data are collected. The controlling can be in the form of 1) issuing periodic visual and audio commands to regularize the respiration motion so that a CT sequence can be formed as a function of the phase of breathing, or 2) using visual and audio commands to prompt the patient to hold breath at specific times and periods as required by the image acquisition process. Although visual signals have been used to prompt patients, use of visual prompting signals have been avoided in radiation procedures. This is because most image devices, such as a computer screen, is too large to fit within the bore of a CT machine. Even for those image devices that could fit within the bore of a CT machine, the image device will take up a lot of space within the bore. This may cause a patient who is confined within a gantry opening to feel uncomfortable—especially if the patient is claustrophobic. Also, electronics of an image device may interfere with a radiation field generated during a CT procedure.

SUMMARY

In accordance with some embodiments, an apparatus for prompting a patient includes a structure configured to be mounted to a patient support, a screen coupled to the structure, and a projector located at a distance away from the screen.

In accordance with other embodiments, a method of prompting a patient that is being supported on a patient support includes adjusting a position of a screen relative to a projector, the screen having a surface, placing the screen in front of the patient such that the patient can see the surface, and providing an image on the screen using the projector.

Other aspects and features will be evident from reading the following detailed description of the preferred embodiments, which are intended to illustrate, not limit, the invention.

BRIEF DESCRIPTION OF THE DRAWINGS

The drawings illustrate the design and utility of various embodiments, in which similar elements are referred to by common reference numerals. In order to better appreciate how advantages and objects of the embodiments are obtained, a more particular description of the embodiments will be illustrated in the accompanying drawings. As such, these drawings depict only embodiments and are not therefore to be considered limiting of its scope.

DETAILED DESCRIPTION OF THE EMBODIMENTS

Figure 1:
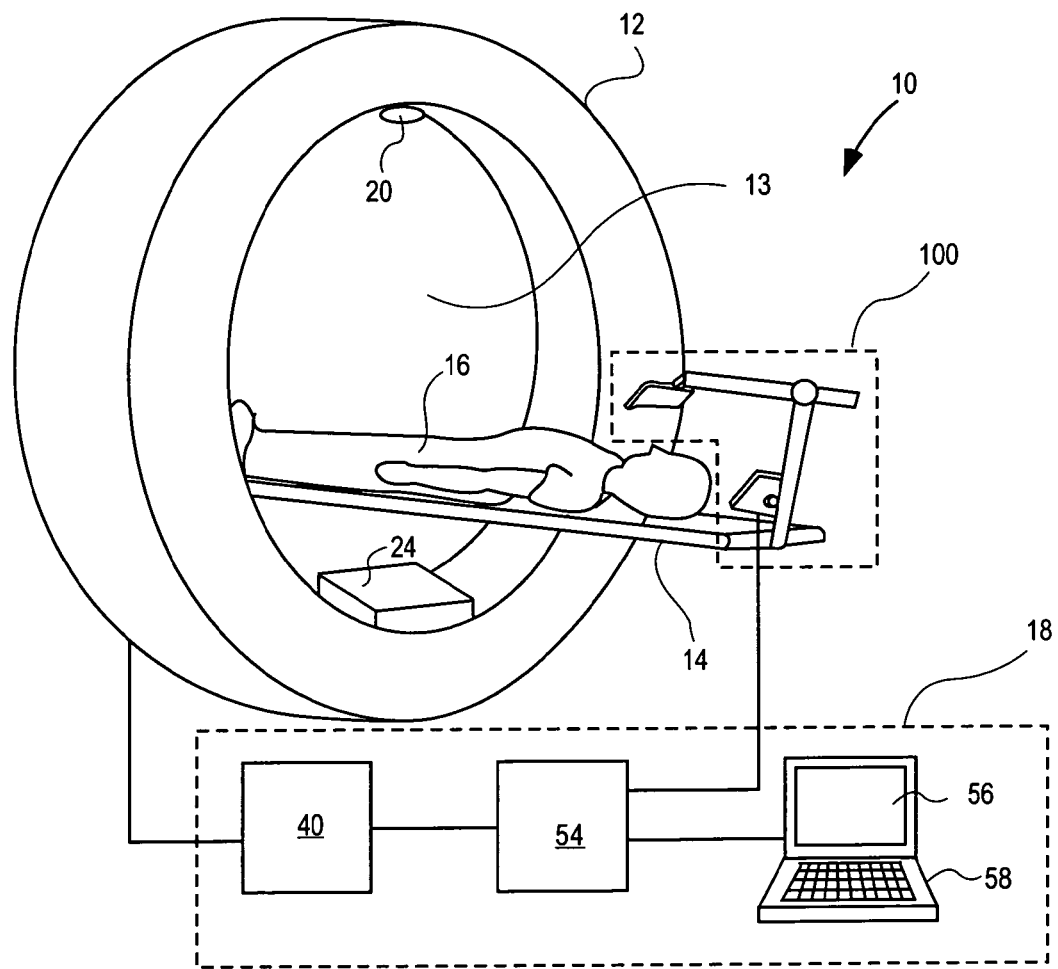
FIG. 1 illustrates a computed tomography system having a patient prompting device in accordance with some embodiments.

Various embodiments are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the invention or as a limitation on the scope of the invention. In addition, an aspect described in conjunction with a particular embodiment is not necessarily limited to that embodiment and can be practiced in any other embodiments.

Referring now to the drawings, in which similar or corresponding parts are identified with the same reference numeral, FIG. 1 illustrates a computed tomography image acquisition system 10, in which embodiments of the present invention can be employed. The system 10 includes a gantry 12 having an opening (or bore) 13, a patient support 14 for supporting a patient 16, and a control system 18 for controlling an operation of the gantry 12. The system 10 also includes an x-ray source 20 that projects a beam of x-rays towards a detector 24 on an opposite side of the gantry 12 while the patient 16 is positioned at least partially between the x-ray source 20 and the detector 24. The detector 24 has a plurality of sensor elements configured for sensing a x-ray that passes through the patient 16. Each sensor element generates an electrical signal representative of an intensity of the x-ray beam as it passes through the patient 16.

In the illustrated embodiment, the control system 18 includes a processor 54, such as a computer processor, coupled to a patient prompting device 100 and to a gantry rotation control 40. The control system 18 may also include a monitor 56 for displaying data and an input device 58, such as a keyboard or a mouse, for inputting data. During a scan to acquire x-ray projection data (i.e., CT image data), the gantry 12 rotates about the patient 16. The rotation of the gantry 12 and the operation of the x-ray source 20 are controlled by the gantry rotation control 40, which provides power and timing signals to the x-ray source 20 and controls a rotational speed and position of the gantry 12 based on signals received from the processor 54. Although the control 40 is shown as a separate component from the gantry 12 and the processor 54, in alternative embodiments, the control 40 can be a part of the gantry 12 or the processor 54. The processor 54 is configured to send prompting signals to the patient prompting device 100 in a prescribed manner (e.g., in synchronization with a rotation of the gantry 12).

Figure 2:
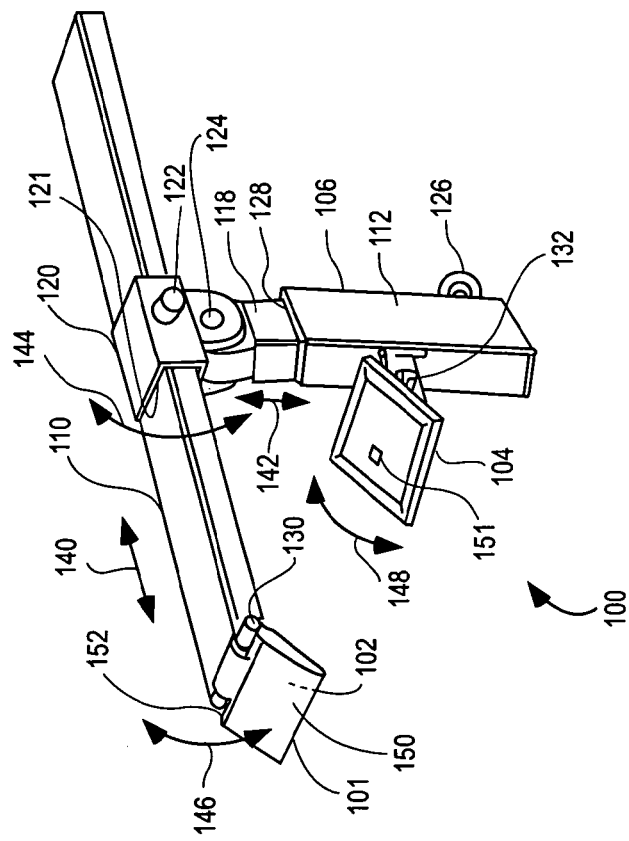
FIG. 2 illustrates a perspective view of the patient prompting device of FIG. 1.

The patient prompting device 100 is configured to provide visual signals to the patient 16 during a procedure, thereby instructing the patient 16 to perform certain task(s). FIG. 2 shows the patient prompting device 100 in accordance with some embodiments of the invention. The patient prompting device 100 includes a screen 101 having a surface 102 between a first side 150 and a second side 152, an image source 104, and a structure 106 to which the screen 101 and the image source 104 are coupled.

In some embodiments, the screen 101 is made from a non-metallic material and does not include circuitry for preventing interference with a radiation field. In other embodiments, the screen 101 may have insubstantial circuitry, which is defined herein as circuitry that does not substantially interfere with the imaging or other treatment procedure being performed. For example, the screen 101 may comprise simple circuits, such as an LED and associated components to provide signals to the patient, that indicate status, etc, such as an LED indicating that the imaging system is on. Depending upon the imaging modality and the ability to tolerate image imperfections, such insubstantial circuitry may be more complex, but stilt comprise substantially less circuitry than a screen such as an LCD screen where the image is formed entirely or substantially from the LCD imaging circuitry. For example, such insubstantial circuitry may form a part of an image or form an image that is overlaid on a projected image.

Figure 3:
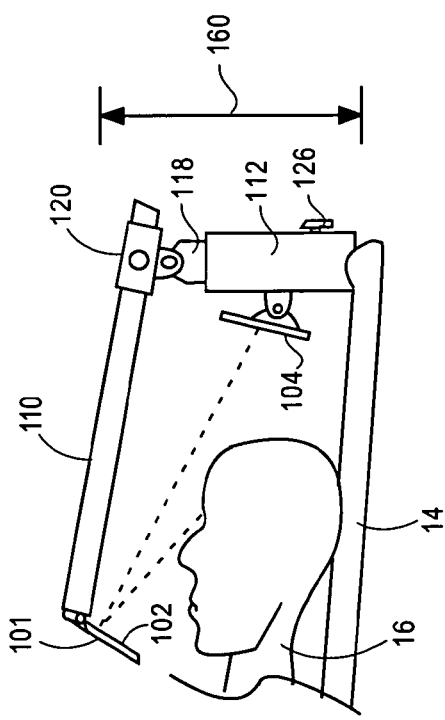
FIG. 3 illustrates a side view of the patient prompting device of FIG. 1, showing the patient prompting device being used to prompt a patient.

In other embodiments, the screen 101 can be any object as long as it provides a surface. In the illustrated embodiments, the surface 102 is a mirror surface, and the image source 104 includes a flat panel screen (or a monitor screen). During use, the image source 104 receives image data from the processor 54 and displays an image 151 in response thereto. The image 151 is reflected by the mirror surface 102, and the patient 16 can see the reflected image 151 by looking towards the mirror surface 102 (FIG. 3). The image 151 displayed on the image source 104 is in reverse (or flipped) such that the patient 16 can see a reflection of the image 151 in a non-reverse (or intended) manner using the mirror surface 102. In the illustrated embodiments, the image 151 provides visual signal to control the patient's breathing (e.g., by instructing the patient 16 to hold breath, to inhale, and/or to exhale). One application is to synchronize the patient breathing to a process being performed by a treatment or imaging device. For example, the patient breathing can be synchronized with a motion of the gantry 12 as the gantry 12 rotates around the patient 16 to collect image data, thereby ensuring that image data that correspond to a prescribed phase of a breathing cycle are obtained. However, in other embodiments, the image 151 can be configured to instruct the patient 16 to perform other task(s), such as, to relax, to move an arm or a leg, to respond to a question, etc.

The above described configuration of the patient prompting device 100 is advantageous because it keeps the electronics of the image source 104 away from a radiation field generated by the x-ray source 20, thereby preventing the electronics of the image source 104 from interfering a CT procedure. Also, it minimizes damage to the image source 104 due to X-ray radiation in a treatment machine. In addition, such configuration provides comfortable viewing of the image 151 because the patient 16 does not need to focus directly onto the image source 104. Also, patients that are far sighted will not need to use reading glasses because reflection through mirror increases a length of the viewing path. Further, the low profile 160 of the prompting device 100 allows the device 100 itself to be placed inside the bore 13 of the CT gantry 12 (or other machines, such as a PET scanner).

The position of the screen 101 can be adjusted relative to the image source 104 to accommodate different patients and/or different applications. In the illustrated embodiments, the structure 106 includes a first arm 110 for carrying the screen 101, a second arm 112 for carrying the image source 104, and connecting members 120, 118 for coupling the first arm 110 to the second arm 112. Particularly, the screen 101 is rotatably coupled to an end of the first arm 110 via a shaft 130, thereby allowing the screen 101 to rotate (as indicated by the arrows 146) relative to the first arm 110. Coupling the screen 101 to the first arm 110 using the second side 152 (i.e., instead of the first side 150) of the screen 101 is advantageous because it allows the first arm 110 to be spaced further from a patient's head, thereby providing more level of comfort to the patient 16. Similarly, the image source 104 is rotatably coupled to the second arm 112 via a shaft 132, thereby allowing the image source 104 to rotate (as indicated by the arrows 148) relative to the second arm 112. The connecting member 120 includes a slot 121 through which the first arm 110 can be inserted, and a knob 122 for securing the first arm 110 relative to the connecting member 120. Such configuration allows the first arm 110 to be translated (in the directions 140), thereby adjusting a position of the screen 101. The connecting member 120 is rotatably secured to the connecting member 118 via a shaft 124, thereby allowing the first arm 110 to rotate relative to the second arm 112 (as indicated by the arrows 144). The connecting member 118 is sized to fit within a lumen 128 of the second arm 112, and is slidable relative to the second arm 112 (as indicated by arrow 142) for adjusting a height of the screen 101. In the illustrated embodiments, the connecting member 118 and the second arm 112 each has a non-circular cross section. However, in alternative embodiments, the connecting member 118 and the second arm 112 can each have a circular cross section, in which case, the connecting member 118 can be rotated about its axis relative to the second arm 112 to place the screen 101 at a desired position. A knob 126 is provided for securing the connecting member 118 relative to the second arm 112 after the connecting member 118 has been desirably positioned. In some embodiments, one or more of the components of the structure 106, such as the first arm 110, the surface, and the joining mechanism, can all be made from a non-metallic material, such as carbon graphite or a polymer, to minimize interference with a radiation field.

The above described structure 106 is advantageous because it allows a position of the screen 101 to be adjusted in multiple directions. However, it should be noted that the structure 106 should not be limited to that described previously, and that the structure 106 can also have other shapes and configurations. For example, in alternative embodiments, the structure 106 can have more or less than two arms (e.g., arms 110, 112). Also, in other embodiments, if two or more arms are provided, one of the arms of the structure 106 can be configured to be moveable or non-moveable relative to another arm, and an orientation of one of the arms relative to another of the arms can be different from that described previously. In addition, in other embodiments, instead of, or in addition to, any of the type of movement characteristics of the screen 101 described previously, the structure 106 can have different number of arms connected by different types of connections to provide desired movement characteristic(s) for the screen 101 (relative to the image source 104 or to the patient support 14). Further, instead of arm(s) or elongated elements, the structure 106 carrying the screen 101 can include other structural elements, such as a block, a plate, a mechanical component, etc. As such, the structure 106 can be any object as long as it is capable of holding the screen 101 at a position relative to the image source 104.

Figure 4:
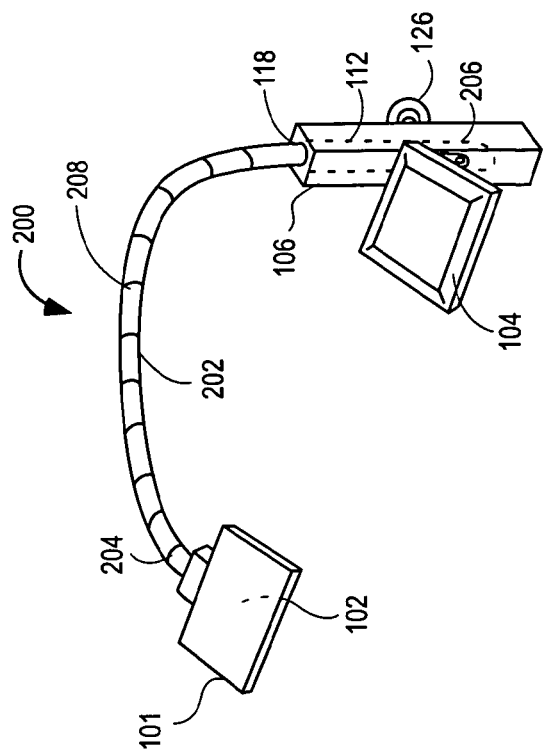
FIG. 4 illustrates a perspective view of a patient prompting device in accordance with other embodiments.
Figure 5:
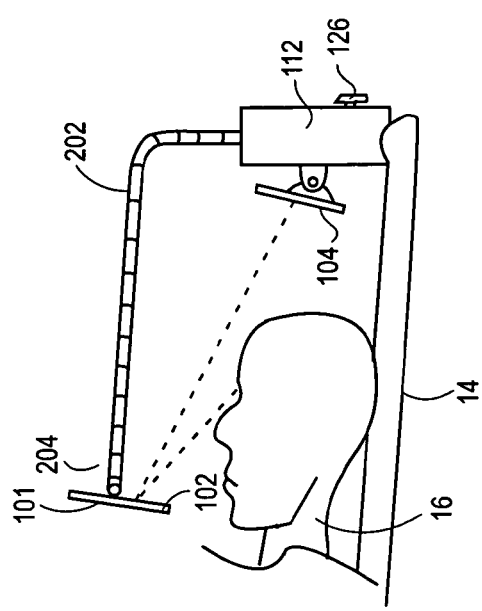
FIG. 5 illustrates a side view of the patient prompting device of FIG. 4, showing the patient prompting device being used to prompt a patient.

FIG. 4 illustrates another patient prompting device 200 in accordance with other embodiments of the invention. Similar to the patient prompting device 100, the patient prompting device 200 includes the screen 101 having the surface 102, and the image source 104. However, unlike the patient prompting device 100, the structure 106 of the patient prompting device 200 does not include the first arm 110. Instead, the structure 106 includes a bellow 202 for holding the screen 101 at a desired position relative to the image source 104. The bellow 202 includes a first end 204 to which the screen 101 is secured, and a second end 206 that is inserted into the lumen 118 of the arm 112. The bellow 202 includes a plurality of segments 208 that can be positioned relative to an adjacent segment 208, thereby allowing the bellow 202 to be bent to a desired profile during use. Such connection is also known as a "goose neck" joint. During use, the image source 104 receives image data from the processor 54 and displays an image 151 in response thereto. The image 151 is reflected by the mirror surface 102, and the patient can see a reflection of the image 151 by looking at the mirror surface 102 (FIG. 5). In alternative embodiments, the structure 106 can include a second bellow for connecting the image source 102 to the arm 112, to the first bellow 208, or to the patient support 14 (in which case, the arm 112 is not required). Also, in other embodiments, instead of using a below, the structure 106 can include another type of bendable element, such as an elastic polymer shaft.

Figure 10:
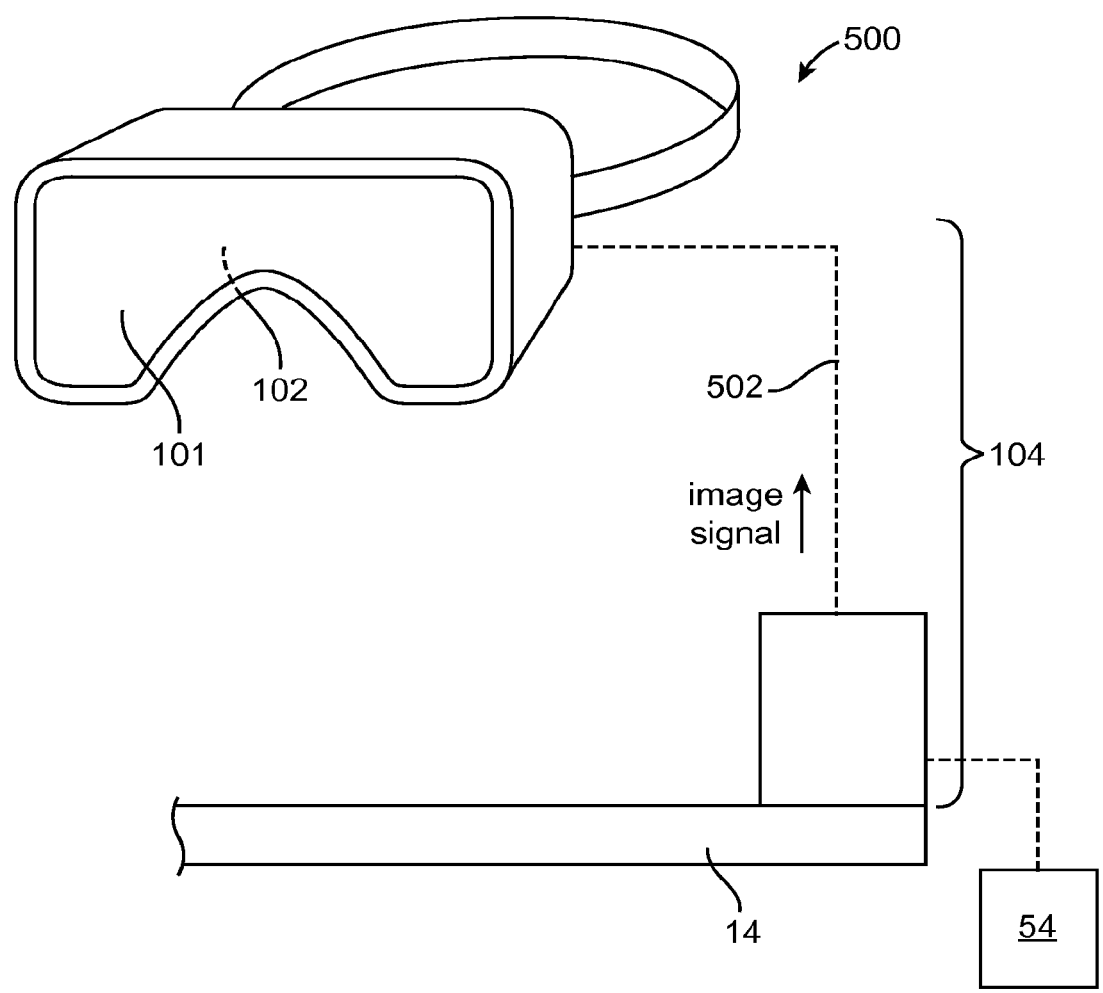
FIG. 10 illustrates a goggles in accordance with some embodiments.
Figure 11:
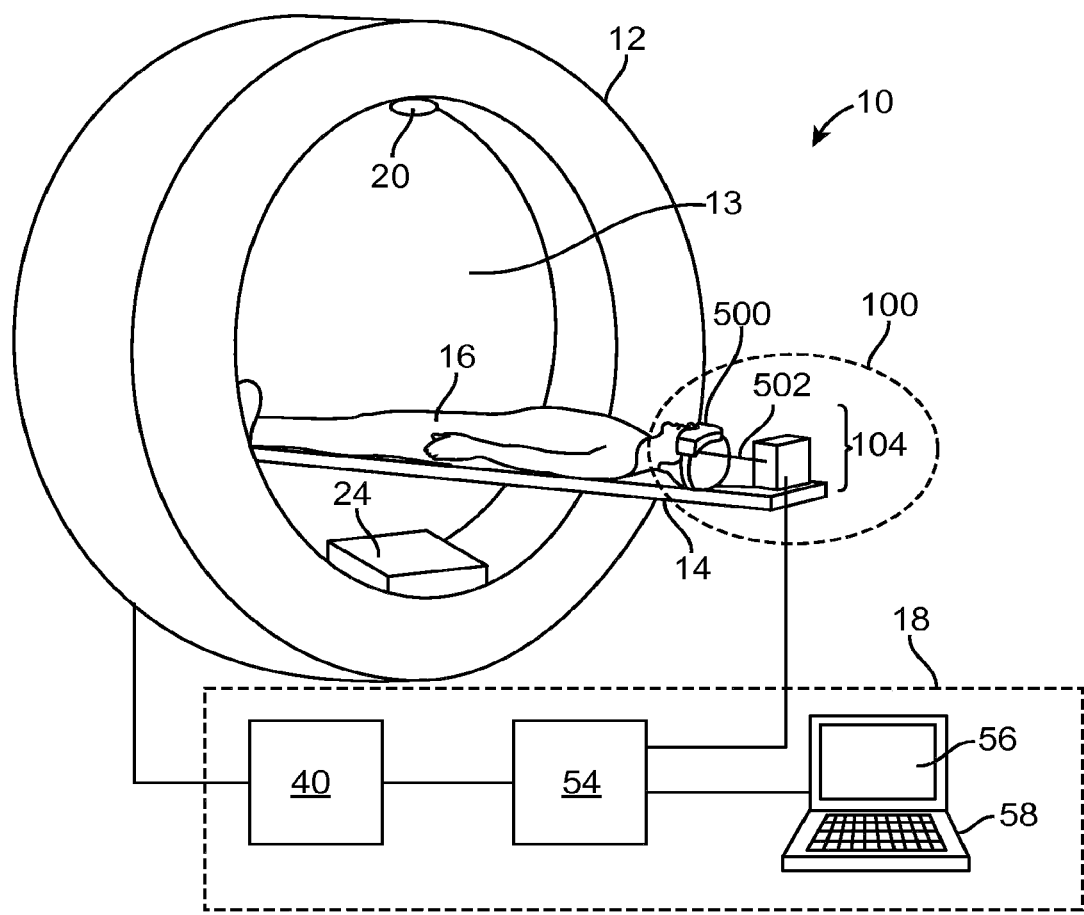
FIG. 11 illustrates the goggles of FIG. 10 being used by a patient.

Although the patient prompting device has been described as having a mirror surface, the scope of the invention should not be so limited. In other embodiments, the patient prompting device can include a non-mirror (e.g., a non-reflective) surface. In such cases, instead of the image source 104 being a flat panel or a screen, the image source 104 includes an image projector that projects image onto the surface 102. Also, in other embodiments, the image source 104 can include fiber optics 502 for transmitting image signals to a viewing surface. In such case, the screen 101 can be a component of a glasses or goggles 500 (FIGS. 10 and 11), with the viewing surface 102 being an inside face of the glasses or goggles 500. Other types of image source can also be used in alternative embodiments.

Figure 6:
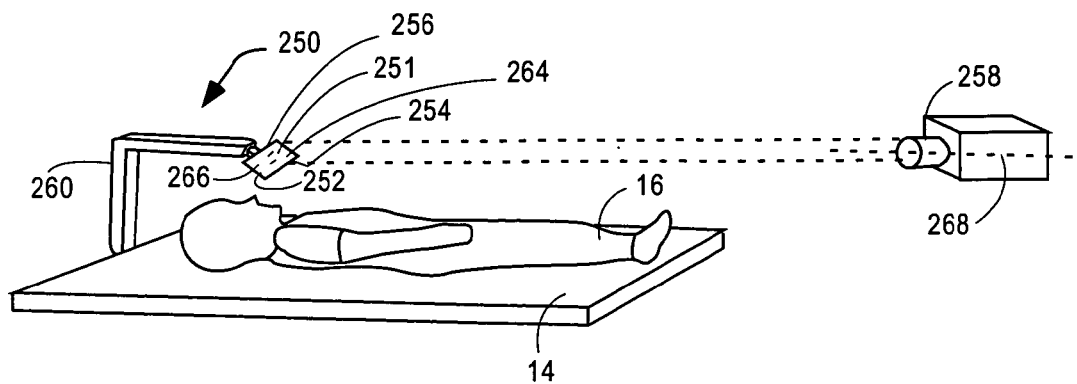
FIG. 6 illustrates a perspective view of a patient prompting device in accordance with other embodiments.

FIG. 6 illustrates a patient prompting device 250 in accordance with other embodiments. The patient prompting device 250 includes a screen 251 having a surface 252 between a first side 254 and a second side 256, an image source 258, and a structure 260 to which the screen 251 and the image source 258 are coupled. The structure 260 can have a configuration that is similar to the structure 106 of FIG. 2 or FIG. 4. In other embodiments, the structure 260 can have other configurations as long as it can secure the screen 251 relative to the patient support 14. In some embodiments, the screen 251 is a non-electronic screen (i.e., does not include circuitry), and made from a non-metallic material, for preventing interference with a radiation field. In other embodiments, the screen 251 includes an insubstantial amount of circuitry (or less) such that the screen 251 does not substantially interfere with an operation of the system 10. For example, in some embodiments, the screen 251 does not include imaging circuitry for a LCD device. In other embodiments, the screen 251 can be any object as long as it provides a surface. In the illustrated embodiments, the screen 251 is a projection screen, and the image source 258 is a projector for back-projecting image(s) to the screen 251.

During use, the image source 258 receives image data from the processor 54 and displays an image in response thereto. The image is projected onto one side 264 of the screen 251, and the patient 16 can see the image by looking towards an opposite side 266 of the screen 251. In the illustrated embodiments, the image provides visual signal to control the patient's breathing (e.g., by instructing the patient 16 to hold breath, to inhale, and/or to exhale). One application is to synchronize the patient breathing to a process being performed by a treatment or imaging device. For example, the patient breathing can be synchronized with a motion of the gantry 12 as the gantry 12 rotates around the patient 16 to collect image data, thereby ensuring that image data that correspond to a prescribed phase of a breathing cycle are obtained. However, in other embodiments, the image can be configured to instruct the patient 16 to perform other task(s), such as, to relax, to move an arm or a leg, to respond to a question, etc.

In the illustrated embodiments, the image source 258 is located at a distance away from the patient 16. Such configuration is advantageous because the electrical components of the image source 258 will not interfere with a radiation field generated during a CT procedure. As shown in the figure, the image source 258 is located adjacent to a bottom of the patient support 14 (where the legs of the patient 16 are supported). Because the screen 251 is tilted such that its surface is non-perpendicular to an axis 268 of the image source 258, a portion of the projected image near the second side 256 will appear larger than another portion of the projected image near the first side 254. In some embodiments, the processor 54 can be configured (e.g., through software/programming) to provide altered image to compensate for a tilting of the screen 251, thereby allowing the patient 16 to view image that appears normal on the screen 251. In other embodiments, the image source 258 can be located at other positions relative to the screen 251. For example, the image source 258 can be positioned such that its axis 268 is substantially perpendicular (e.g., 90°±10°) to the surface of the screen 251. In such cases, the image as it appears on the screen 251 will appear normal to the patient 16.

Figure 7:
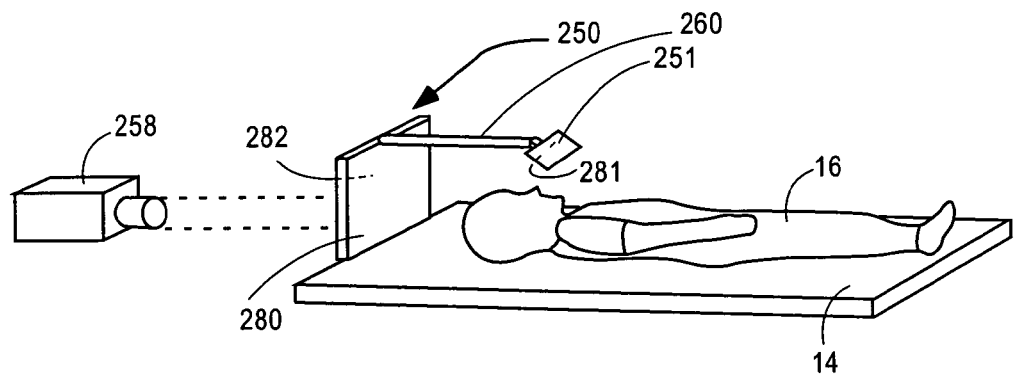
FIG. 7 illustrates a perspective view of a patient prompting device in accordance with other embodiments.

FIG. 7 illustrates a variation of the embodiments of FIG. 6, in which the image source 258 is located adjacent to a top of the patient support 14 (where the head of the patient 16 is supported). In such cases, the patient prompting device 250 further includes a projection screen 280, and the screen 251 includes a mirror surface 281. During use, the image source 258 receives image data from the processor 54 and displays an image in response thereto. The image is projected onto one side 282 of the projection screen 280, and the patient 16 can see the image by looking towards the mirror surface 281 of the screen 251. As similarly discussed herein, in some embodiments, the processor 54 can optionally be configured (e.g., through software/programming) to provide altered image to compensate for a tilting of the screen 251, thereby allowing the patient 16 to view image that appears normal on the screen 251.

In the embodiments of FIGS. 6 and 7, the image source 258 is secured to the patient support 14 (e.g., through a mechanical arm or connection). Such configuration is advantageous in that it allows the image source 258 to move together with the patient support 14 as the patient support 14 is being positioned. In other embodiments, the image source 258 can be secured to other objects, such as a wall, a ceiling, a CT machine or any of other objects adjacent to the patient support 14. In such cases, the processor 54 and/or the image source 258 can be configured to adjust a zooming and a focusing of the image(s) as the patient support 14 is being positioned relative to the image source 258.

Figure 8:
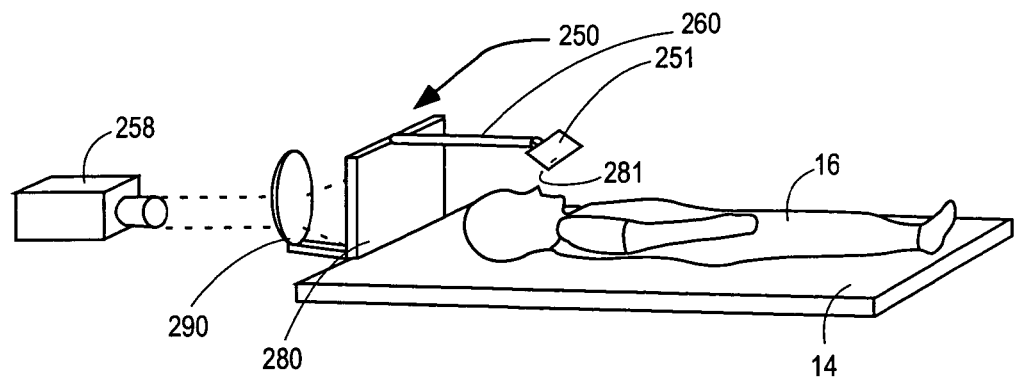
FIG. 8 illustrates a perspective view of a patient prompting device having a focusing device in accordance with other embodiments.

FIG. 8 illustrates another variation of the patient prompting device 250 in which the patient prompting device 250 further includes a focusing device 290 located between the image source 258 and the projection screen 280. In some embodiments, the focusing device 290 may include a set of lenses in a telescopic arrangement such as those found in modern cameras, or a two-dimensional lens array that is known in the art. In such cases, the image source 258 is not secured to the patient support 14, and is configured to focus image(s) at a far distance (e.g., at a distance that is between 5 feet and infinity, and more preferably, more than 20 feet, away from the image source 258). The focusing device 290 is secured relative to the projection screen 280 such that it will move together with the projection screen 280 as the patient support 14 is being positioned. The focusing device 290 will focus image(s) correctly onto the projection screen 280 regardless of the distance between the image source 258 and the projection screen 280.

In other embodiments, the patient prompting device 100, 200, or 250 can further include a connection mechanism for connecting the structure 106 to the patient support 14. The connection mechanism can include, for examples, a clamp, a screw knob, or a pull-and-release type knob. In some cases, the connection mechanism can include one or more members connected to the structure 106 for mating with respective receiving members on the patient support 14. In other embodiments, the patient prompting device 100 or 200 can further include the patient support 14, in which case, the prompting device 100 or 200 can be fixedly secured to the patient support 14 (e.g., via a weld, a bolt, or a screw), or be detachably secured to the patient support 14.

Figure 9:
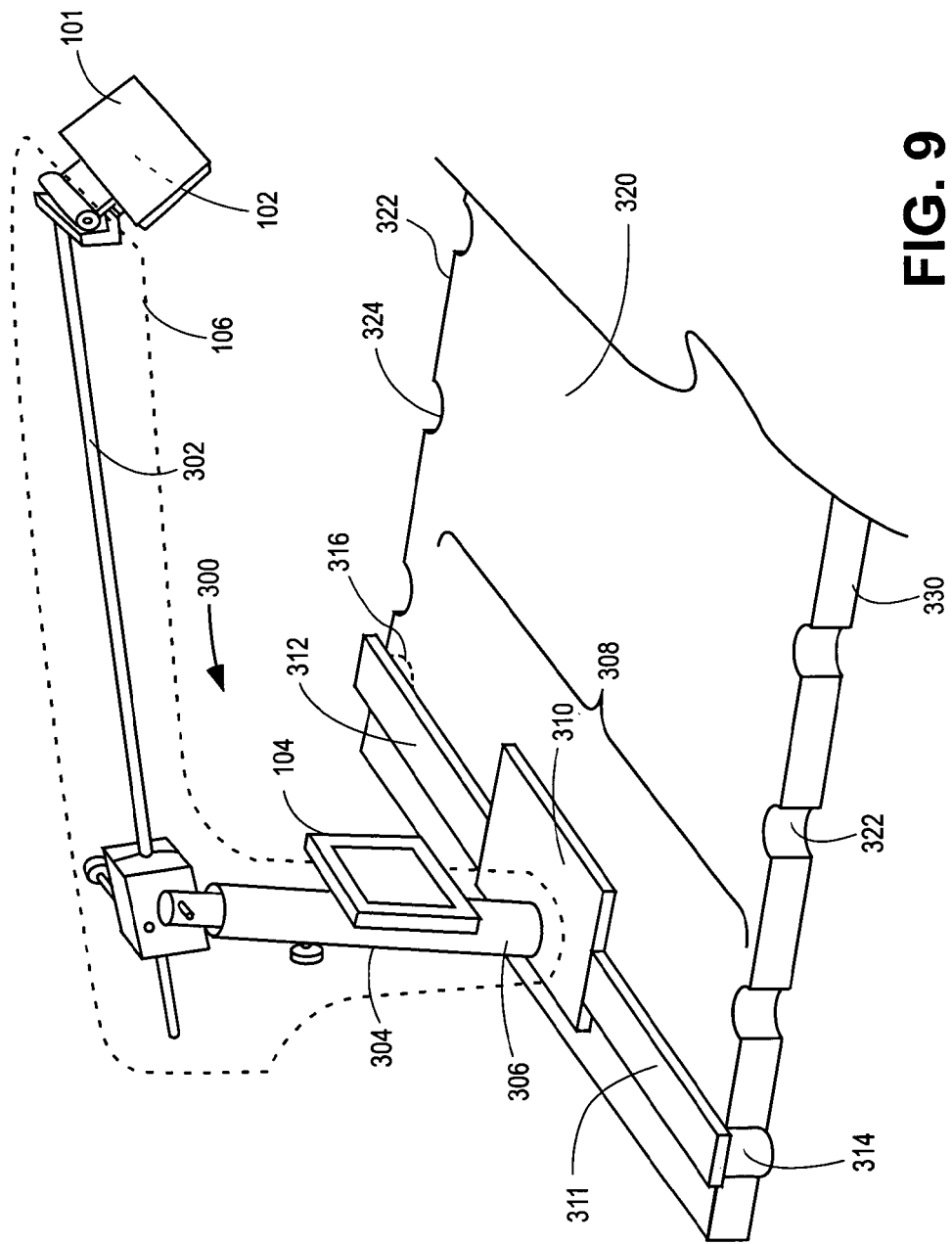
FIG. 9 illustrates a perspective view of a patient prompting device in accordance with other embodiments.

FIG. 9 illustrates a patient prompting device 300 that is configured to be detachably secured to a patient support 320. The patient prompting device 300 includes the screen 101, the image source 104, and the structure 106, and is similar to the patient prompting device 100 described previously. The structure 106 includes a rod 302 (first arm) coupled to a support 304 (second arm), with the support 304 having an end 306 that is attached to a securing mechanism 308. The securing mechanism 308 includes a plate 310, members 311, 312 extending from the plate 310, and securing elements 314, 316 located at respective ends of the members 311, 312. The securing elements 314, 316 can be, for example, circular disks, or other types of fastening members. In the illustrated embodiments, the patient support 304 includes a plurality of recesses 322 on a first edge 330, and a plurality of recesses 324 on a second edge 332. The securing elements 314, 316 are configured to mate with the one of the recesses 322 and one of the recesses 324, respectively, on both sides of the patient support 320. The plurality of recesses 322, 324 allow a position of the patient prompting device 300 be adjusted relative to the support 320. The securing mechanism 308 and the patient support 320, and variations thereof, have been described in U.S. Pat. No. 5,806,116, the entire disclosure of which is expressly incorporated by reference herein.

Also, in some embodiments, the patient prompting device 100 can include a processor, such as the processor 54, for processing image signals/data. Further, in other embodiments, the patient prompting device 100 or 200 can further include one or more speakers for providing audio signal to the patient 16 in addition to the visual signal 50. For example, the speaker(s) can be integrated speaker(s) that is part of the image source 104. Alternatively, the speaker(s) can be separate speaker(s) that is secured to the structure 106 or to the patient support 14. In addition, in other embodiments, the image source 104 can be configured to receive audio and/or video signals by one or more wireless connections. In such cases, the image source 104 includes its own power source and a wireless receiver for receiving signals from a transmitter.

Figure 12:
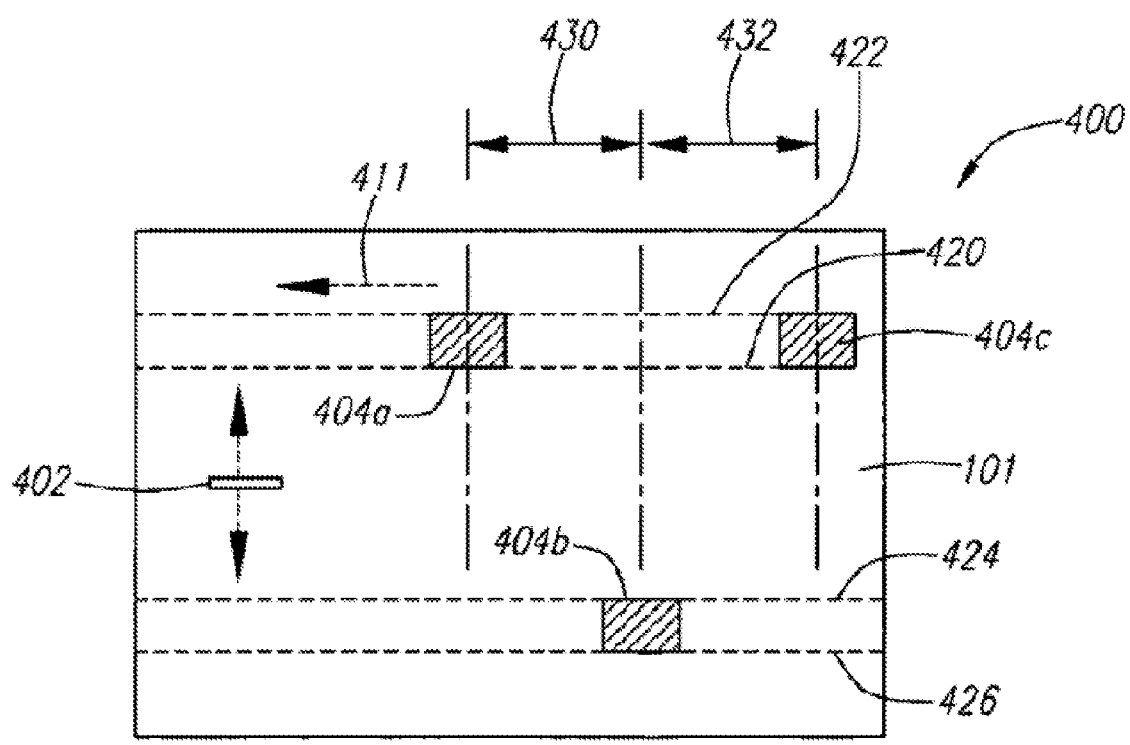
FIG. 12 illustrates an example of a user interface for prompting a patient to inhale and exhale in accordance with some embodiments.

FIG. 12 illustrates an example of a user interface for prompting a patient to inhale and exhale in accordance with some embodiments. As shown in FIG. 12, the first target 404a represents a prescribed inhale level desired to be accomplished by the patient 16. The target 404a has bottom and top sides that correspond to a minimum inhale level 420 and a maximum inhale level 422, respectively. Similar is true for the target 404c. The second target 404b represents a prescribed exhale level desired to be accomplished by the patient 16. The target 404b has top and bottom sides that correspond to a minimum exhale level 424 and a maximum exhale level 426, respectively. In some embodiments, the distances (e.g., distances, 430, 432) between successive targets 404 can be adjusted, depending on a particular need of a procedure. Also, in other embodiments, a length of a target can be adjusted, e.g., made longer to indicate that a breath-hold is desired. In some embodiments, the prescribed inhale level, the prescribed exhale level, and the distances 430, 432 are user specific, and can be determined during a training session. Such will make the patient more comfortable because the interface is prescribing a manner of breathing in which the patient is accustomed to performing.

During use of the interface 400, the targets 404 move in a direction indicated by arrow 411 (see FIG. 12), and in synchronization with a rotation of the gantry 12 (or the radiation source 20). The patient 16 is instructed (either before or during a radiation procedure) to move the first indicator 402 to intercept the targets 404, e.g., one after the other, by inhaling and exhaling, as the targets 404 moves across the screen 101, thereby controlling substantially all phases of the patient's breathing cycle. Such result is particularly desirable in the case in which sets of image data are desired to be collected for different prescribed phases of a breathing cycle, which requires patient breathing period to be as constant as possible and the phase of the periodic breathing motion to be synchronized with the gantry angle at any given time. In the illustrated embodiments, the processor 54 is configured to activate the radiation source 20 to generate image data when the first indicator 402 intercepts a target (one of the targets 404), and deactivate the radiation source 20 when the first indicator 402 misses a target. In some embodiments, a physician can prescribe a number N of phases into which a breathing cycle is divided. In such cases, the processor 54 is configured to provide appropriate visual signals via the patient prompting interface 400, and to provide timing signals to the gantry control 40 such that sets of image data for each of the N prescribed phases of a breathing cycle can be collected.

Although embodiments of the patient prompting device have been described as being used with the computed tomography image acquisition system 10, in alternative embodiments, any of the embodiments of the patient prompting device described herein can be used to control patient motion in other types of radiation process. For examples, instead of a CT procedure, any of the above described patient prompting devices can be used in a laminar tomography procedure, a MRI procedure, a PET procedure, or other imaging procedures. Also, in other embodiments, instead of using the patient prompting device in image acquisition procedures, any of the above described patient prompting devices can be used in a treatment procedure, such as a radiation treatment procedure that requires a synchronization of a patient's movement to a treatment machine. In addition, in further embodiments, any of the embodiments of the patient prompting device described herein can be used in different applications, which may or may not require use of a radiation machine.

Although particular embodiments have been shown and described, it will be understood that they are not intended to limit the present inventions, and it will be obvious to those skilled in the art that various changes and modifications may be made without departing from the spirit and scope of the present inventions. For example, in other embodiments, instead of securing the image source 104 to the structure 106, the image source 104 can be secured to the patient support 14, or to another structure that is coupled to the patient support 14. In such cases, the patient prompting device 100 or 200 does not include the image source 104. Also, in other embodiments, the image source 104 is not limited to a single flat panel screen, a single monitor screen, or a single projector, and can include multiple image-providing devices (e.g., multiple flat panel screens, monitor screens, or projectors). For example, multiple image-providing devices can be used to provide 2-dimensional projection or holographic. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method of providing information to a patient that is being supported on a patient support, comprising:
   providing a screen for viewing by the patient; and
   providing an image on the screen using a device, wherein the image has (1) a first object indicating a desired inhale level to be achieved and (2) a patient-controlled item that moves in response to a breathing movement of the patient;
   wherein the first object comprises a discrete block that moves relative to the screen in a first direction, the patient-controlled item being moveable relative to the screen in a second direction that is different from the first direction; and
   wherein the patient-controlled item is moveable in the second direction to intercept the first object that moves in the first direction.

2. The method of claim 1, wherein the image also has a second object prescribing an exhale level.

3. The method of claim 1, wherein a position of the first object with respect to the screen indicates a prescribed time in a future at which to achieve the desired inhale level.

4. The method of claim 1, wherein the object has a first side and a second side, and a distance between the first and second sides of the first object indicates a duration for which to maintain the desired inhale level.

5. The method of claim 1, wherein the screen is non-metallic.

6. The method of claim 1, wherein the screen is a part of an eyewear.

7. The method of claim 1, wherein the act of providing the image comprises using fiber optics to transmit the image from the device.

8. The method of claim 1, wherein the first object comprises a first vertical line that moves across at least a part of the screen.

9. The method of claim 8, wherein the first object comprises a second vertical line representing a prescribed time at which the desired inhale level is no longer needed to be achieved.

10. The method of claim 9, wherein the first vertical line and the second vertical line are parts of a rectangular block.

11. The method of claim 8, wherein the image further includes a second object having a second vertical line representing a prescribed time for achieving the desired exhale level, wherein the first object and the second object are spaced apart from each other in the screen.

12. The method of claim 1, wherein the first object indicates the desired inhale level to be achieved by indicating a constant range of inhale levels that includes the desired inhale level.

13. The method of claim 1, wherein at least a part of the first object has a rectilinear configuration.

14. An apparatus for providing information to a patient, comprising:
- a screen with a first surface for viewing by the patient, and a second surface that is opposite from the first surface; and
- a device located at a distance away from the screen, wherein the device is configured to provide an image for display on the first surface of the screen, wherein the image has (1) a first object indicating a desired inhale level to be achieved and (2) a patient-controlled item that moves in response to a breathing movement of the patient;
- wherein the first object comprises a discrete block that moves relative to the screen in a first direction, the patient-controlled item being moveable relative to the screen in a second direction that is different from the first direction; and
- wherein the patient-controlled item is moveable in the second direction to intercept the first object that moves in the first direction.

15. The apparatus of claim 14, wherein the image also has a second object prescribing an exhale level.

16. The apparatus of claim 14, wherein a position of the first object with respect to the screen indicates a prescribed time in a future at which to achieve the desired inhale level.

17. The apparatus of claim 14, wherein the first object has a first side and a second side, and a distance between the first and second sides of the first object indicates a duration for which to maintain the desired inhale level.

18. The apparatus of claim 14, wherein the screen is non-metallic.

19. The apparatus of claim 14, wherein the screen is a part of an eyewear.

20. The apparatus of claim 19, wherein the device comprises a projector, and wherein the apparatus further comprises a projection screen to which the device is configured to project the image, wherein the screen of the eyewear comprises a mirror surface for displaying a reflection of the image.

21. The apparatus of claim 19, wherein the eyewear comprises a pair of glasses.

22. The apparatus of claim 19, wherein the eyewear comprises a goggles.

23. The apparatus of claim 14, further comprising fiber optics for transmitting the image from the device.

24. The apparatus of claim 14, wherein the device is configured for providing backprojected images.

25. The apparatus of claim 14, wherein the screen comprises a non-mirror surface.

26. The apparatus of claim 14, wherein the device is secured to a patient support.

27. The apparatus of claim 14, further comprising a focusing device for focusing the image provided by the device.

28. The apparatus of claim 14, further comprising a processor coupled to the device.

29. The apparatus of claim 28, wherein the processor is configured to cause the device to display the image for instructing the patient to move a body part.

30. The apparatus of claim 14, wherein the image comprises a visual signal for prompting the patient to control a breathing the patient.

31. The apparatus of claim 14, wherein the screen is translatable relative to the device.

32. The apparatus of claim 14, wherein the screen is rotatable relative to the device.

33. The apparatus of claim 14, wherein the device comprises a projector.

34. The apparatus of claim 14, wherein the screen comprises a flat surface.

35. The apparatus of claim 14, wherein the image is configured for instructing the patient to control a breathing of the patient such that the breathing corresponds with a process being performed by a treatment device or an imaging device.

36. The apparatus of claim 14, wherein the image is configured for instructing the patient to control a breathing of the patient such that the breathing corresponds with a motion of a gantry that rotates around the patient.

37. The apparatus of claim 36, wherein the gantry is a part of a CT machine.

38. The apparatus of claim 14, wherein the first object comprises a first vertical line that moves across at least a part of the screen.

39. The apparatus of claim 38, wherein the first object comprises a second vertical line representing a prescribed time at which the desired inhale level is no longer needed to be achieved.

40. The apparatus of claim 39, wherein the first vertical line and the second vertical line are parts of a rectangular block.

41. The apparatus of claim 38, wherein the image further includes a second object having a second vertical line representing a prescribed time for achieving the desired exhale level, wherein the first object and the second object are spaced apart from each other in the screen.

42. The apparatus of claim 14, wherein the first object indicates the desired inhale level to be achieved by indicating a constant range of inhale levels that includes the desired inhale level.

43. The apparatus of claim 14, wherein at least a part of the first object has a rectilinear configuration.

* * * * *